(12) United States Patent
Cobley et al.

(10) Patent No.: US 10,905,895 B2
(45) Date of Patent: Feb. 2, 2021

(54) LIPOLYSIS RADIATION PADDLE

(71) Applicant: LASER LIPO LTD, Edenbridge (GB)

(72) Inventors: Ian Cobley, Edenbridge (GB); Sharon Cobley, Edenbridge (GB)

(73) Assignee: LASER LIPO LTD., Edenbridge (GB)

( * ) Notice: Subject to any disclaimer, the term of this patent is extended or adjusted under 35 U.S.C. 154(b) by 69 days.

(21) Appl. No.: 15/977,567

(22) Filed: May 11, 2018

(65) Prior Publication Data

US 2018/0339168 A1 Nov. 29, 2018

(30) Foreign Application Priority Data

May 24, 2017 (GB) .................................. 1708294.2

(51) Int. Cl.
*A61B 18/20* (2006.01)
*A61N 5/06* (2006.01)
(Continued)

(52) U.S. Cl.
CPC .......... *A61N 5/0616* (2013.01); *A61B 18/203* (2013.01); *A61B 18/22* (2013.01); *A61N 5/0625* (2013.01); *A61B 2018/00005* (2013.01); *A61B 2018/00452* (2013.01); *A61B 2018/00464* (2013.01); *A61N 7/00* (2013.01);
(Continued)

(58) Field of Classification Search
CPC ...... A61N 5/06; A61N 5/0616; A61N 5/0625; A61N 7/00; A61N 2005/005; A61N 2005/0643; A61N 2005/0644; A61N 2005/0645; A61N 2005/0647; A61N 2005/0652; A61N 2005/0659; A61N 2005/0662; A61N 2005/067; A61N 2007/0008; A61B 18/203; A61B 18/22;
(Continued)

(56) References Cited

U.S. PATENT DOCUMENTS 7,975,702 B2 7/2011 Cho et al.
2002/0123743 A1 9/2002 Shanks et al.
(Continued)

FOREIGN PATENT DOCUMENTS

CN 203777380 U 8/2014
CN 103479428 B 1/2016
(Continued)

OTHER PUBLICATIONS

GB 1708294.2 Search Report under Section 17, dated Nov. 3, 2017.
EP 18 17 1400.7-1124 Extended European Search Report, dated Oct. 25, 2018.

*Primary Examiner* — Ankit D Tejani
*Assistant Examiner* — Joshua Brendon Solomon
(74) *Attorney, Agent, or Firm* — Fay Sharpe LLP (57) ABSTRACT

A lipolysis radiation paddle (2) comprises a plurality of lipolysis radiation transducers (14) mounted in a base (20). The base (20) has a lower portion (21), and a pair of side portions (26) extending upwardly from respective sides of the lower portion (21). The lower portion (21) is shaped to fit under the jaw (51) of a user (50) of the paddle (2), and has a front end (22) shaped to receive the chin (52) of the user (50). The side portions (26) are each shaped to extend to and along respective sides of the jawline (53) of the user (50). The transducers (14) are directed inwardly towards the skin in proximity to the paddle (2).

15 Claims, 5 Drawing Sheets

(51) Int. Cl.
*A61B 18/22* (2006.01)
*A61N 7/00* (2006.01)
*A61N 5/067* (2006.01)
*A61B 18/00* (2006.01)
*A61N 5/00* (2006.01)

(52) U.S. Cl.
CPC .. *A61N 2005/005* (2013.01); *A61N 2005/067* (2013.01); *A61N 2005/0643* (2013.01); *A61N 2005/0644* (2013.01); *A61N 2005/0645* (2013.01); *A61N 2005/0647* (2013.01); *A61N 2005/0652* (2013.01); *A61N 2005/0659* (2013.01); *A61N 2005/0662* (2013.01); *A61N 2007/0008* (2013.01)

(58) Field of Classification Search
CPC .......... A61B 2018/00005; A61B 2018/00452; A61B 2018/00464
See application file for complete search history.

(56) References Cited

U.S. PATENT DOCUMENTS

| | | |
|---|---|---|
| 2004/0162549 A1* | 8/2004 | Altshuler ............. A61B 18/203 606/9 |
| 2011/0264083 A1 | 10/2011 | Welches et al. |
| 2014/0081359 A1 | 3/2014 | Sand |
| 2014/0379052 A1 | 12/2014 | Myeong et al. |
| 2015/0051671 A1 | 2/2015 | Browne |
| 2015/0190652 A1 | 7/2015 | George |
| 2016/0310756 A1 | 10/2016 | Boll et al. |
| 2017/0136263 A1* | 5/2017 | Reil ....................... A61B 18/18 |
| 2017/0266461 A1 | 9/2017 | Boll et al. |

FOREIGN PATENT DOCUMENTS

| | | |
|---|---|---|
| EP | 2 431 001 A1 | 3/2012 |
| EP | 2 431 002 A1 | 3/2012 |
| GB | 2536192 A | 9/2016 |
| KR | 10-2012-0103250 A | 9/2012 |
| WO | WO 2015/167213 A1 | 11/2015 |
| WO | WO 2016/209857 A1 | 12/2016 |
| WO | WO 2017/180663 A1 | 10/2017 |

* cited by examiner

LIPOLYSIS RADIATION PADDLE

The present invention relates to a lipolysis radiation paddle for applying lipolysis radiation to a user.

Radiation induced lipolysis results in fat cells in the body of the user having their cell walls ruptured, whereby fat is released and dissipated in the body. The radiation is applied by transducers such as laser diodes. A device for applying the radiation may comprise a plurality of laser diodes mounted on a printed circuit board (PCB). The diodes and the PCB are housed in a casing from which the laser diodes can radiate light into the user's body for disruptive influence on fat cells. The device may be known as a lipolysis radiation paddle. The lipolysis radiation paddle is typically used to dissipate fat formed in areas of the body which are relatively smooth such as the thigh, buttocks and stomach. It is necessary for the paddle to fit closely adjacent the area where the fat cells are located. Conventional paddles are not suitable for relatively angular areas of the body such as the face and neck primarily because all the laser diodes mounted on a single PCB cannot be brought into functional proximity with the body at one time, and trying to use the paddle on such areas is liable to result in long and inefficient application of radiation. Furthermore, use of these conventional paddles on the face or neck may cause laser irradiation of the eyes of the user which is potentially dangerous.

Where the transducers are laser diodes, then these laser diodes can increase in temperature as they are being used which can cause their power to decrease.

It is an object of the present invention to provide a lipolysis radiation paddle to alleviate at least one of the above-mentioned problems.

According to the present invention there is provided a lipolysis radiation paddle which comprises a plurality of lipolysis radiation transducers mounted in a base, wherein the base has a lower portion, and a pair of side portions extending upwardly from respective sides of the lower portion, and the lower portion is shaped to fit under the jaw of a user of the paddle, and has a front end shaped to receive the chin of the user, and the side portions are each shaped to extend to and along respective sides of the jawline of the user, the transducers directed inwardly towards the skin in proximity to the paddle. The transducers are configured to induce lipolysis in fat cells under said skin around and below the jaw.

The shape of the lipolysis radiation paddle enables the transducers to effectively apply radiation to fat cells in a lower facial area or jaw area of the user when the paddle is properly positioned. The radiation reduces/disperses unwanted fat in this area. The transducers may apply radiation to preplatysma and jowl fat cells of the user. The radiation reduces/disperses unwanted fat under the chin which is often known as a double chin. Use of the paddle on the user is non-invasive. The front end of the lower portion of the base enables the paddle to be properly positioned by being shaped to receive the chin. The shape of the paddle also prevents the eyes of the user from being irradiated.

The front end of the lower portion of the base may be shaped so as to accommodate at least a lower part of the chin of the user.

The paddle may include a cover covering the base and the transducers, the cover comprising a material that enables the lipolysis radiation transducers to emit lipolysis radiation through it. The cover covering the base is arranged to engage with the skin of the user when the paddle is applied to the jaw area of the user. The cover prevents the skin of the user from touching the transducers and protects the transducers from contamination from, say, sweat or dirt on the user's skin.

The cover may extend over the front end and is arranged to engage with the skin of the lower part of the chin when the paddle is applied to the user.

The abutment of the chin of the user with the front end, which may be covered, determines the location of the paddle on the face of the user so that the transducers are positioned to apply radiation to the required fat cells.

The base may include a rear portion which extends outwardly and/or downwardly from a rear end of the lower and side portions. The rear portion of the base may be shaped to fit against upper front side portions of the neck of the user. The rear portion may comprise a pair of wings separated by a gap positioned so as to accommodate the Adam's apple of the user when the paddle is applied to the user. The rear portion may include a plurality of lipolysis radiation transducers mounted therein, the transducers directed towards the skin in proximity to the rear portion. The transducers are configured to induce lipolysis in fat cells under the skin in the neck area when the paddle is applied to the user. In particular, fat deposits may be reduced on the upper front side portions of the neck of the user. The gap in the rear portion prevents the Adam's apple from being irradiated by the transducers, and also the larynx and thyroid gland from being irradiated by the transducers. The rear portion may also have a cover or the rear portion may be covered by the cover.

Each lipolysis radiation transducer may comprise a sonic transducer such as an ultrasonic transducer or an electromagnetic transducer such as a radio frequency transducer or an infra-red, visible light or ultra-violet transducer. Each lipolysis radiation transducer may comprise a light emitting diode or a laser diode. The paddle may include a power supply circuit board to which at least one chain of laser diodes is connected.

The paddle may include a cooling apparatus for cooling the paddle. The cooling apparatus may cool the laser diodes so that they do not heat up and thus lose power. The cooling apparatus may comprise a network of vents for receiving cooling fluid. The cooling fluid may be air which may be at room temperature. The network of vents may comprise a plurality of apertures extending through the base. The network of vents may comprise at least one conduit for providing cooling fluid between the cover and the base.

The base of the paddle may be rigid. Its shape and size enables treatment to be applied to users with different sized jaws, chins and necks. The base may comprise aluminium.

A lipolysis radiation applicator may be provided which includes a paddle as described above, and a control system for controlling power to the transducers in the paddle. The applicator may include a pump for pumping cooling fluid into the network of vents in the paddle. The control system of the applicator may also be for controlling the pump.

The applicator may include a transducer mounted in a holder, the transducer being connected to the control system, and the holder configured to be attached to the user so that the transducer is directed towards the skin. The transducer is configured to irradiate a lymph gland under said skin.

An embodiment of the present invention will now be described, by way of example, with reference to the accompanying schematic drawings, in which.

Figure 1:
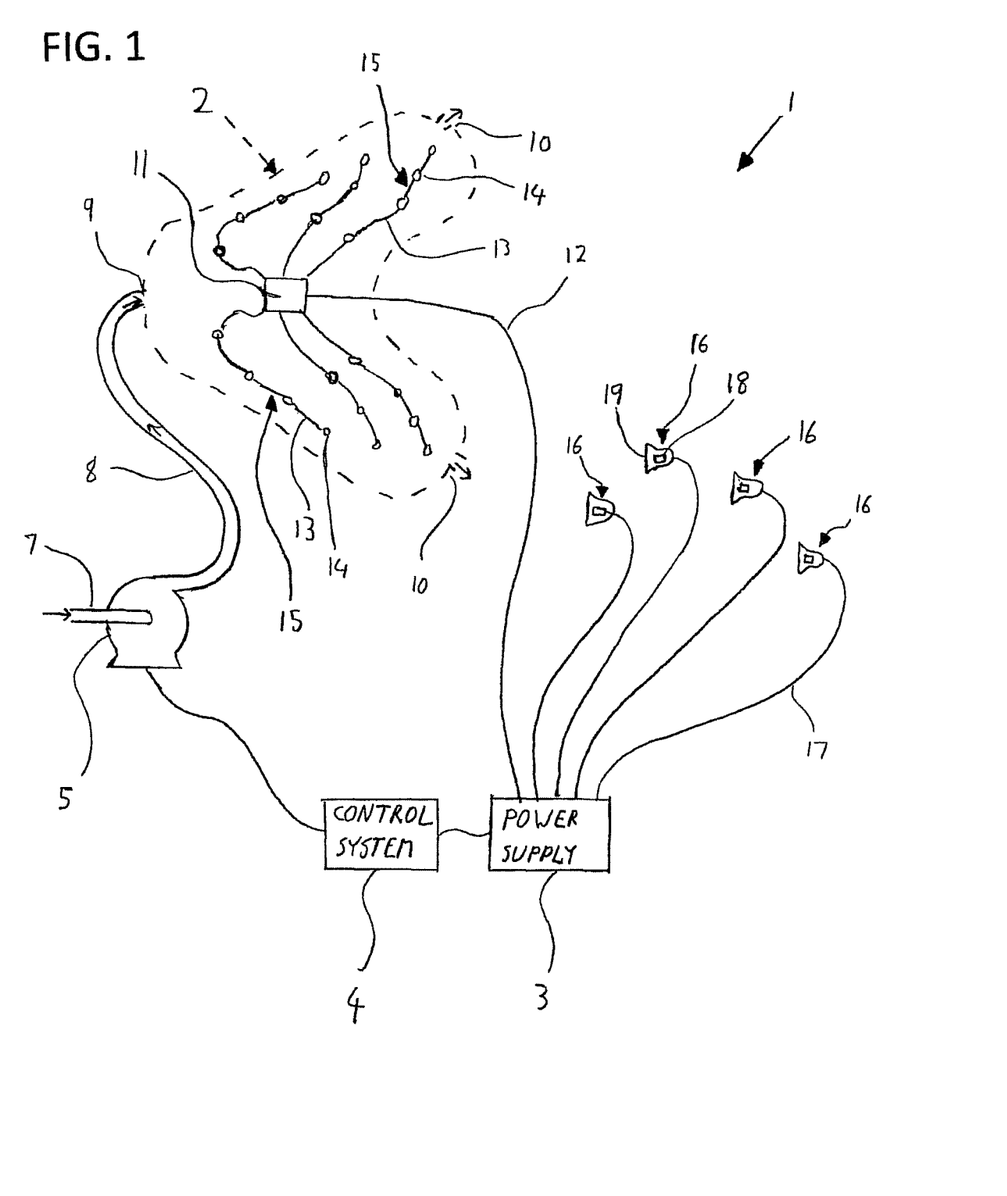
FIG. 1 is a view of a lipolysis radiation applicator including a lipolysis radiation paddle in accordance with one embodiment of the present invention.

Referring to FIG. 1 of the accompanying drawings, a lipolysis radiation apparatus 1 comprises a lipolysis radiation paddle 2, and a power supply 3 with a control system or main control unit 4 connected thereto.

The control system 4 is connected to a pump 5 which has a pump inlet port 7 and a pump outlet conduit 8. The pump outlet conduit 8 is connected to an air inlet port 9 of the lipolysis radiation paddle 2, and the paddle 2 also has air outlet ports 10.

The power supply 3 is connected to a printed circuit board (PCB) 11 in the lipolysis radiation paddle 2 by a power cable 12. Further cables 13 extend from the PCB 11 and each of these cables 13 connects a plurality of laser diodes 14 in series as a daisy chain 15 wherein the daisy chains 15 are inside the paddle 2, and power can be provided to the laser diodes 14 from the power supply 3 via the PCB 11. At least some of the laser diodes 14 may alternatively be connected in parallel.

The power supply 3 may also have a plurality of cluster probes 16 connected to it by respective cables 17. Each cluster probe 16 contains a single laser diode 18 housed in a medical grade cover or holder 19 suitable to be placed against the skin, and is shaped to be able to deliver the desired radiation to a user or subject. The cluster probes 16 are also shaped so that they feel comfortable on the user when they are attached to the user.

Referring to FIGS. 2 to 8, the lipolysis radiation paddle 2 comprises a metal base or mask 20 having a substantially flat lower portion 21 for being positioned under a jaw of the user. A front end 22 of the lower portion 21 is inclined upwards from a main part 23 of the lower portion 21. When the main part 23 of the lower portion 21 is horizontal, the front end 22 is at a shallow angle 81 of, say, between 10° and 20° to the horizontal. The front end 22 is shaped to receive the chin of the user. The front end 22 has a curved shape with the apex 24 of the curve being on a longitudinal centre line 25 of the base 20. A pair of side portions 26 extends upwardly from respective sides of the lower portion 21. Each side portion 26 is curved upwards from the main part 23 of the lower portion 21. Each side portion 26 tapers towards the front end 22 of the lower portion 21. An outer edge 27 of each side portion 26 is inclined from the front end 22 to an upper rear end 28 of each side portion 26 in a direction away from the lower portion main part 23. The upper rear end 28 of each side portion 26 extends slightly rearward beyond a rear end 29 of the lower portion 21. A rear portion 30 of the base 20 extends away from the rear end 29 of the lower portion 21 and a rear edge 31 of each side portion 26 which extends between the rear ends 28 and 29. The rear portion 30 extends outwardly from the lower portion 21 and the side portions 26. The rear portion 30 is inclined downwardly from the rear end 29 of the lower portion 21. The rear portion 30 is inclined at a shallow angle $\theta_2$ of, say, between 5° and 25° to the horizontal when the lower portion main part 23 is in a horizontal orientation.

An outer edge 35 of the rear portion 30 has a central concave section, which provides a recess or gap 32 extending into the rear portion 30, the recess 32 being centred on the longitudinal centre line 25. The recess 32 has a curved shape with its apex 33 on the longitudinal centre line 25. The part of the rear portion 30 on either side of the recess 32 forms a wing or flap 34. Each wing 34 also has a curved shape curving away from the recess 32 so that the outer edge 35 of the wings 34 and recess 32 forms a wave shape. The lower portion 21, side portions 26 and rear portion 30 of the base 20 form an integral unit.

The base 20 has a plurality of apertures 36 for holding the laser diodes 14 in the lower portion 21, the side portions 26 and the wings 34. The apertures 36 extend through the base 20 from an outer side 37 of the base 20 to an opposite inner side 38 of the base 20 which is to face the user's skin when the base 20 is applied to the user. The end of each aperture 36 at the outer side 37 has an annular flange or shoulder 39 on which a respective said laser diode 14 is placed. A top end of the laser diode 14 is flush with the inner side 38 or recessed by no more than 2 mm from the inner side 38. The annular flange 39 surrounds an opening 40 and cabling for each laser diode 14 extends through the opening 40. The apertures 36 and their laser diodes 14 are substantially uniformly distributed over the lower portion 21, the side portions 26 and the wings 34.

Figure 2:
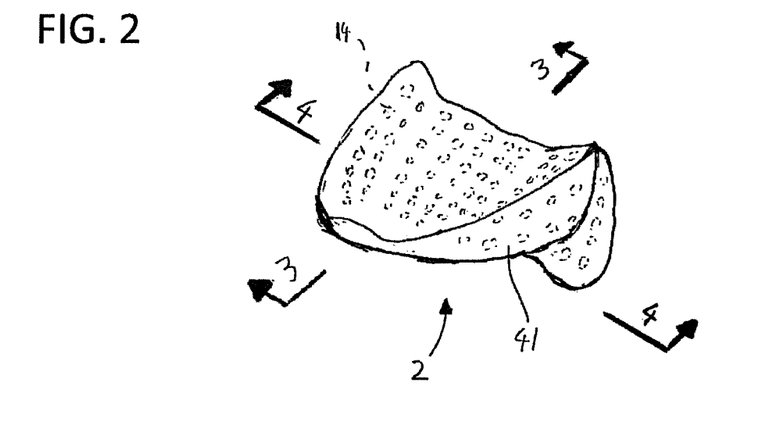
FIG. 2 is a perspective view of the lipolysis radiation paddle.
Figure 3:
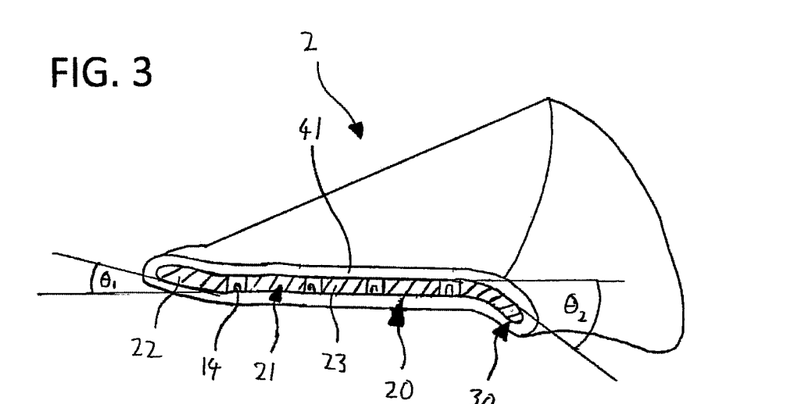
FIGS. 3 and 4 are sectional views taken along lines 3-3 and 4-4, respectively, of FIG. 2.
Figure 4:
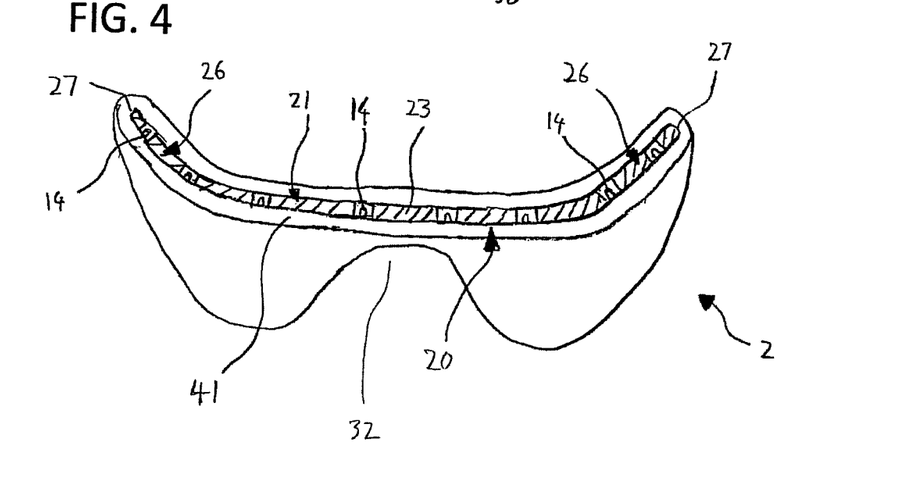
Figure 5:
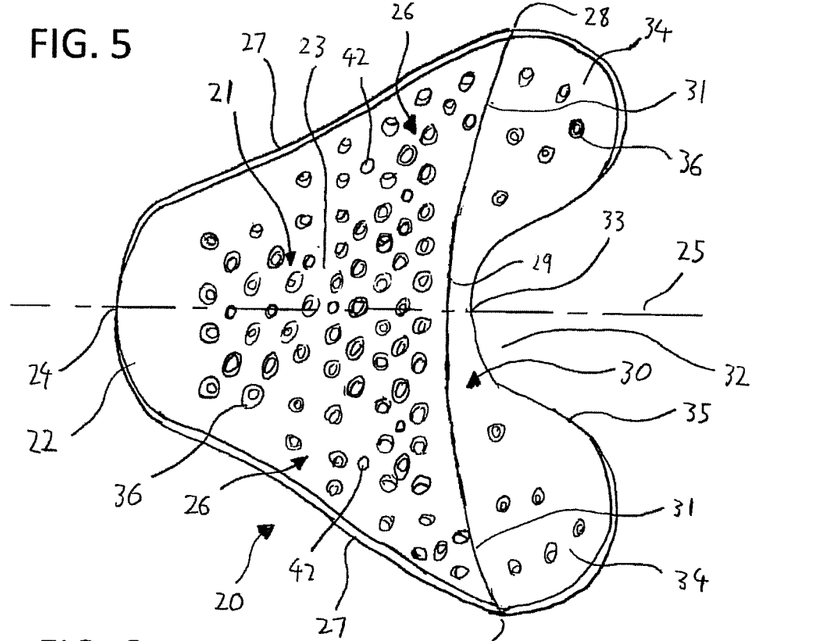
FIGS. 5 and 6 a plan view and a side elevational view, respectively, of a base of the lipolysis radiation paddle.
Figure 6:
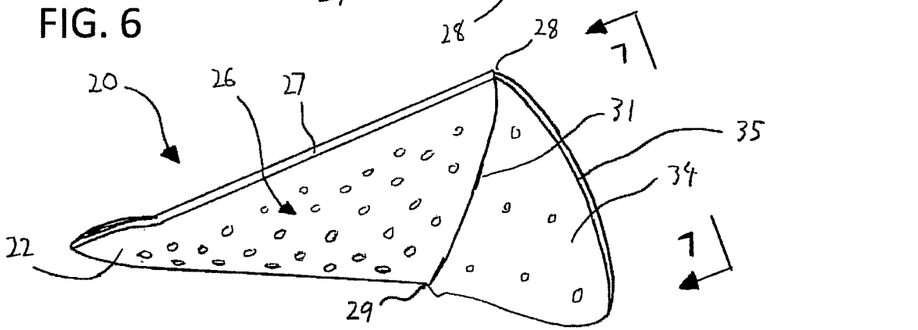
Figure 7:
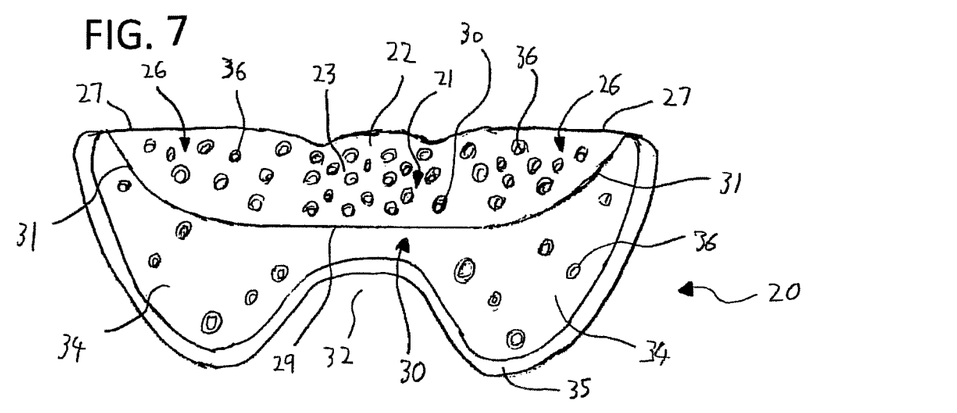
FIG. 7 is a rear view of the base taken along lines 7-7 of FIG. 6.
Figure 8:
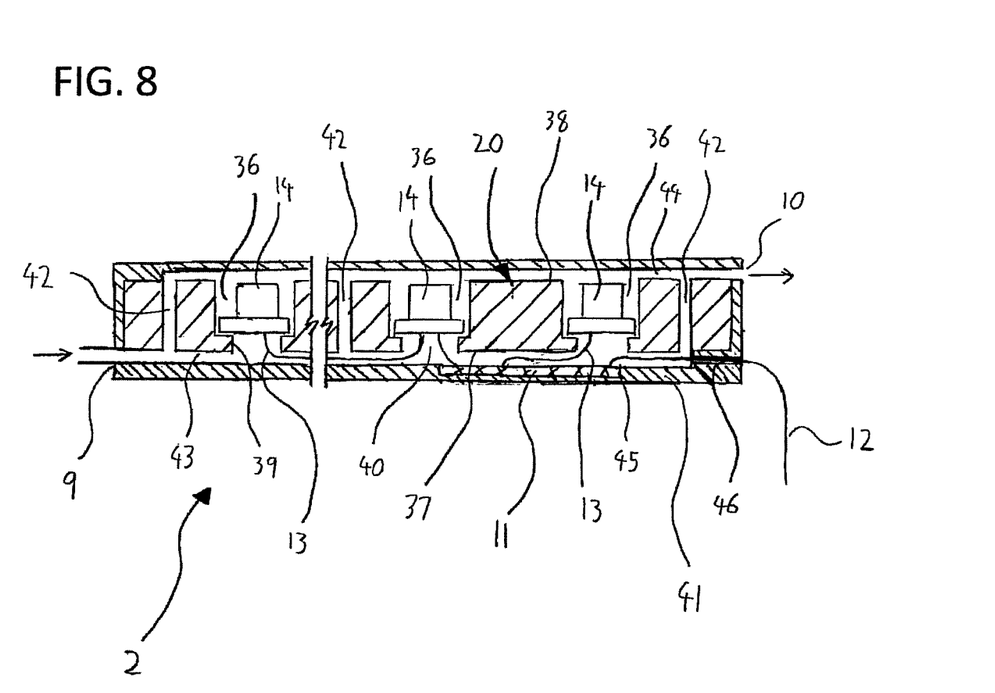
FIG. 8 is a representational cross-sectional view of the lipolysis radiation paddle.

Once the laser diodes 14 have been placed in the base 20, the base 20 is covered by an optically clear acrylic cover or casing 41 which holds the laser diodes 14 in place, and through which the laser diodes 14 can irradiate the skin of the user of the paddle 2.

A plurality of vents 42 extends between the outer and inner sides 37, 38 of the base 20. The ends of the vents 42 at the outer side 37 are connected by channels 43 in the cover 41 to the air inlet port 9, and the ends of the vents 42 at the inner side 38 are connected by channels 44 in the cover 41 to the air outlet ports 10.

The cover 41 has a recess 45 for holding the PCB 11 and channels for housing the cables 13 for the daisy chains 15. At least part of at least some of the cables 13 may be housed in some of the channels 43 for connecting the vents 42 to the air inlet port 9. The cover 41 also has a cable inlet port 46 through which the power cable 12 to the PCB 11 from the power supply 3 passes.

Figure 9:
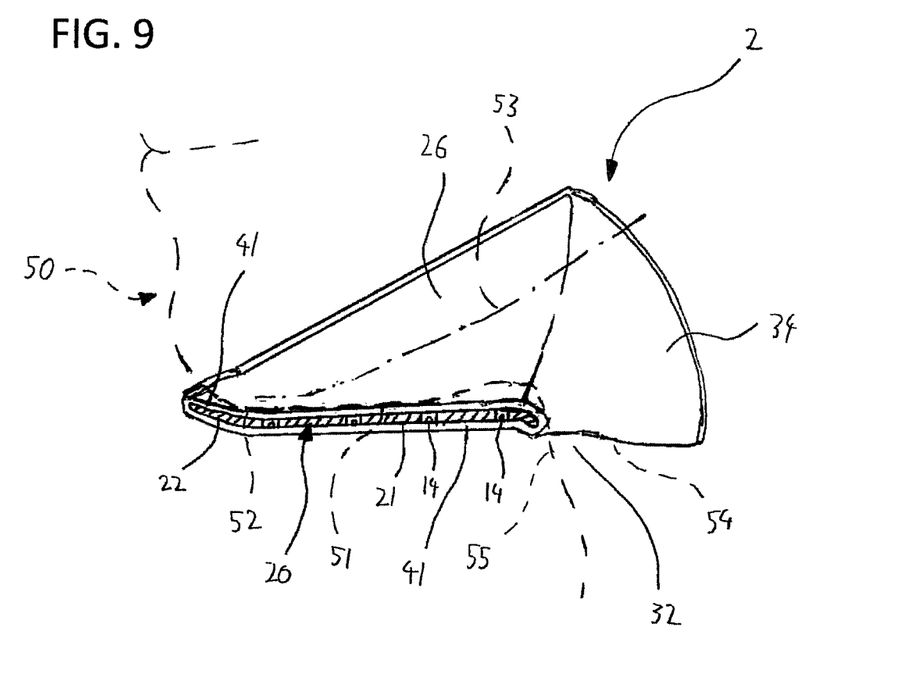
FIG. 9 is a sectional view of the lipolysis radiation paddle against a chin and neck of a user of the paddle.

In use, the lipolysis radiation paddle 2 is applied to the user or subject 50 so that the covered lower portion 21 fits under the jaw 51 of the user 50 and the covered front end 22 of the lower portion 21 receives a lower part of the chin 52 of the user 50 to determine the exact position of the paddle 2 on the face of the user 50 (see FIG. 9). The covered side portions 26 each extend to and along respective sides of the jawline 53 of the user 50, and the covered wings 34 of the rear portion 30 of the base 20 are adjacent upper front side portions 54 of the neck of the user 50, the gap 32 between the wings 34 positioned so as to accommodate the Adam's apple 55 of the user 50. Downward pressure of the user's face pushes the skin of the user 50 against the paddle 2 so that at least a portion of the cover 41 which extends over the front end 22 engages the skin of the lower part of the chin 52. Most of an inside surface of the cover 41 should engage the lower face of the user 50. If a user 50 has an undershot jaw and a prominent Adam's apple, then the position of the paddle 2 on the user 50 may be determined by the covered wings 34 engaging the upper front side portions 54 of the neck on either side of the Adam's apple 55.

One or more supporting arms may hold the paddle 2 in place on the face of the user 50. The paddle 2 may alternatively be held in place by a hand or by straps or other appropriate means.

The cluster probes 16 are placed over lymph glands in the neck, shoulders and upper body of the user 50 and are held in place by surgical tape or other suitable means.

The control system 4 controls power supplied from the power supply 3 to the paddle laser diodes 14 via the PCB 11 wherein power is supplied to the laser diodes 14 for a specified period of time. The laser diodes 14 in the lower portion 21 and side portions 26 of the base 20 are directed inwardly towards the skin of the user 50 to induce lipolysis in preplatysma fat cells in the jaw and jowl fat cells, respectively. The laser diodes 14 in the wings 34 of the rear portion 30 are directed to induce lipolysis in preplatysma fat cells in the upper neck. The paddle 2 is sized and shaped to hold the laser diodes 14 and to determine the position of the paddle 2 on the face of the user 50 so that the laser diodes 14 are positioned to apply radiation to the required fat cells. The area of the paddle containing the laser diodes 14 to face the user is an operative region.

Fat released by the laser diodes 14 in the paddle 2 may accumulate in the lymph glands in the neck, shoulders and upper body of the user 50. The control system 4 controls power supplied from the power supply 3 to the laser diodes 18 of the cluster probes 16. Irradiation by the cluster probes 16 of these lymph glands assists in the fat being dispersed from these glands and metabolised by the body of the user 50.

The control system 4 also operates the pump 5 to pump air at room temperature adjacent the pump inlet port 7 into the network of vents 42 in the paddle 2 via the air inlet port 9 to cool the laser diodes 14, and controls the amount of air pumped into the paddle 2. The pumped air escapes from the paddle 2 via the air outlet ports 10. Instead of air, other cooling fluid or solutions could be pumped into the network of vents 42.

The base 20 can be made from various materials other than metal such as plastics. The cover 41 may be a flexible material. The cover 41 can be made of a material that can be safely placed against the skin of a user. The flexible material may be created with gas injection, moulds or machined materials.

In a specific example of a preferred embodiment, there are 15 laser diodes 14 in at least most of the daisy chains 15, with there being at least 110 laser diodes 14 provided in the paddle 2. There may be about 8 daisy chains 15. Preferably, there would be between 100 and 140 laser diodes 14 or other transducers in the paddle 2. Although it is convenient to use an even number of daisy chains 15, an odd number could instead be used. Any suitable number of daisy chains 15 may be used. Each wing 34 of the base rear portion 30 may have between 5 and 10 laser diodes 14. The light irradiated by each laser diode 14, 18 may have a wavelength between 550 and 700 nm. The paddle 2 may be supplied with power between 27 and 120 mW. The laser diodes 14, 18 are to be between 2 and 5 mm from the skin of the user. The base 20 has approximately 8 vents 42, and 20 to 40 litres of air per minute may be pumped through the paddle 2 to cool the laser diodes 14. The treatment time is between 10 and 20 minutes. The cover 41 may be a medical grade clear PVC material. The metal base 20 may be of aluminium. The metal base 20 may be between 5 and 10 mm thick. The lipolysis radiation apparatus 1 may include four cluster probes 16.

Whilst a particular embodiment has been described, it will be understood that various modifications may be made without departing from the scope of the claimed invention. The rear portion 30 may be optional. The paddle may have a single air outlet port. At least parts of the paddle may be shaped to extend significantly beyond the operative region.

The invention claimed is:

1. A lipolysis radiation paddle which comprises:
   a plurality of lipolysis radiation transducers mounted in a base,
   wherein the base has a lower portion, and a pair of side portions extending upwardly from respective sides of the lower portion, and the lower portion is shaped to fit under the jaw of a user of the paddle, and has a front end shaped to receive the chin of the user, and the side portions are each shaped to extend to and along respective sides of the jawline of the user, the transducers directed inwardly towards the skin in proximity to the paddle,
   wherein the base includes a rear portion which extends outwardly from a rear end of the lower and side portions,
   wherein the rear portion of the base is shaped to fit against upper front side portions of the neck of the user,
   wherein the rear portion comprises a pair of wings which extends downwardly from the rear end of the lower and side portions and are separated by a gap positioned so as to accommodate the Adam's apple of the user when the paddle is applied to the user, and
   wherein the wings include a plurality of lipolysis radiation transducers mounted therein, the transducers directed towards the skin in proximity to the wings when the paddle is applied to the user.

2. The paddle as claimed in claim 1, wherein the front end is shaped so as to accommodate at least a lower part of the chin of the user.

3. The paddle as claimed in claim 1, including a cover covering the base and the transducers, the cover comprising a material that enables the lipolysis radiation transducers to emit lipolysis radiation through it.

4. The paddle as claimed in claim 3, wherein the cover extends over the front end.

5. The paddle as claimed in claim 1, wherein the rear portion is covered by a cover which also covers the base and the transducers, the cover comprising a material that enables the lipolysis radiation transducers to emit lipolysis radiation through it.

6. The paddle as claimed in claim 1, wherein each lipolysis radiation transducer comprises a laser diode.

7. The paddle as claimed in claim 6, including a power supply circuit board to which at least one chain of laser diodes is connected.

8. The paddle as claimed in claim 1, including a cooling apparatus for cooling the paddle.

9. The paddle as claimed in claim 8, wherein the cooling apparatus comprises a network of vents for receiving cooling fluid.

10. The paddle as claimed in claim 9, wherein the network of vents comprises a plurality of apertures extending through the base.

11. The paddle as claimed in claim 9, wherein the network of vents comprises at least one conduit for providing cooling fluid between the base and a cover covering the base and the transducers, the cover comprising a material that enables the lipolysis radiation transducers to emit lipolysis radiation through it.

12. A lipolysis radiation applicator including a paddle as claimed in claim 1, and a control system for controlling power to the transducers in the paddle.

13. The applicator as claimed in claim 12, including a cooling apparatus comprising a network of vents, and the applicator including a pump for pumping cooling fluid into the network of vents in the paddle for cooling the paddle.

14. The applicator as claimed in claim 13, wherein the control system is also for controlling the pump.

15. The applicator as claimed in claim 12, including a transducer mounted in a holder, the transducer being connected to the control system, and the holder configured to be attached to the user so that the transducer is directed towards the skin.

\* \* \* \* \*